United States Patent
Zardi et al.

(10) Patent No.: US 8,158,823 B2
(45) Date of Patent: Apr. 17, 2012

(54) METHOD FOR THE MODERNIZATION OF A UREA PRODUCTION PLANT

(75) Inventors: Federico Zardi, Breganzona (CH); Andrea Scotto, Breganzona (CH)

(73) Assignee: Urea Casale S.A. (CH)

( * ) Notice: Subject to any disclaimer, the term of this patent is extended or adjusted under 35 U.S.C. 154(b) by 170 days.

(21) Appl. No.: 12/464,518

(22) Filed: May 12, 2009

(65) Prior Publication Data

US 2009/0292140 A1 Nov. 26, 2009

(30) Foreign Application Priority Data

May 20, 2008 (EP) .................................... 08009267

(51) Int. Cl.
*C07C 273/00* (2006.01)
(52) U.S. Cl. ................. 564/67; 564/69; 564/70; 564/71
(58) Field of Classification Search ................... 564/67, 564/69, 70, 71
See application file for complete search history.

(56) References Cited

U.S. PATENT DOCUMENTS

| 5,660,801 A | 8/1997 | Pagani et al. |
| 5,886,222 A | 3/1999 | Rescalli |
| 7,279,599 B2 | 10/2007 | Pennino |
| 2002/0035292 A1 | 3/2002 | Mennen et al. |
| 2002/0188157 A1* | 12/2002 | Fukunaka et al. ............... 564/72 |
| 2005/0256339 A1* | 11/2005 | Zardi ............... 564/66 |
| 2010/0217041 A1* | 8/2010 | Carlessi et al. ................ 564/70 |

FOREIGN PATENT DOCUMENTS

| GB | 1542371 | 3/1979 |
| WO | 2006/061083 A1 | 6/2006 |

* cited by examiner

*Primary Examiner* — Jafar Parsa
(74) *Attorney, Agent, or Firm* — Akerman Senterfitt

(57) ABSTRACT

A method for revamping a conventional self-stripping urea plant is disclosed, where a minor portion (18a) of the carbon dioxide feed is fed to the stripper (7) and used as a stripping agent. In further embodiments, another carbamate condenser is installed, or the conventional horizontal shell-and-tube carbamate condenser (6) is replaced with a vertical submerged unit.

13 Claims, 2 Drawing Sheets

METHOD FOR THE MODERNIZATION OF A UREA PRODUCTION PLANT

FIELD OF THE INVENTION

The present invention discloses a method for revamping and increasing the capacity of a self-stripping urea plant.

PRIOR ART

The self-stripping or thermal-stripping process is a well known process for the synthesis of urea. It is often referred to as the Snamprogetti process, having been developed by Snamprogetti in the late 60s. A disclosure of the process and related plant can be found for example in GB 1542371. Many urea plants are using this process worldwide.

Basically, the self-stripping process provides reaction between ammonia and $CO_2$ in a high pressure reactor around 150-160 bar and N/C ratio usually around 3.2-3.4 molar; the solution containing ammonia and unconverted ammonium carbamate discharged by the reactor is heated in a high-pressure stripper to decompose the carbamate and recover ammonia. A vapour phase containing ammonia and $CO_2$ produced in the stripper is condensed in a high-pressure condenser, which is part of a high-pressure loop together with the reactor and stripper, and recycled to said reactor. Usually the plant comprises a medium-pressure and a low-pressure decomposition section to further separate urea from unconverted ammonia and carbamate.

The main equipments of a urea plant operating with the self-stripping process are the following:
- a high-pressure synthesis reactor fed with ammonia and carbon dioxide, and producing a mixture comprising urea, carbamate and free ammonia in aqueous solution;
- a steam-heated high-pressure stripping section, receiving said mixture and providing partial decomposition of the carbamate and partial separation of free ammonia, obtaining a vapour phase comprising ammonia and carbon dioxide and an aqueous solution comprising urea, residual carbamate and ammonia;
- a medium-pressure section where said solution comprising urea, residual carbamate and ammonia is heated, partially decomposing the carbamate and separating the ammonia;
- a low-pressure recovery section, receiving urea and residual carbamate obtained in said medium-pressure section, and further decomposing the carbamate and separating residual ammonia;
- a high-pressure condensing section comprising at least one horizontal condenser, condensing the vapour phase from the stripping section and thus obtaining a liquid stream comprising recycled carbamate in aqueous solution, which is fed to the reactor.

The stripping section comprises at least one stripper where the aqueous solution from the reactor is fed to a steam-heated tube bundle, without additional use of a stripping gas. Heat supplied by the steam results in the partial decomposition of the carbamate into carbon dioxide and ammonia which, together with part of the free ammonia contained in said mixture, are recovered at the top of the stripping unit, condensed in said horizontal condenser and then recycled to the reactor. Ammonia can also be used as a stripping agent in the self-stripping plants.

The condenser of a conventional self-stripping urea plant is a shell-and-tube horizontal unit of kettle type, where the gaseous phase is condensed on the tube side in the presence of the recycled carbamate solution recovered from the medium- or low-pressure section and used as a condensation liquid. The condensation heat is used to produce steam.

There is an ever increasing interest in revamping the existing self-stripping urea plants, operating with the above process. In this specification, the term "revamping" indicates the modification of an existing plant, in order to improve its performance and obtain, for example, a larger production capacity and/or a better conversion yield, or else to reduce energy consumption.

The self-stripping process however has some drawbacks, that may have a negative influence also on the possibility of an attractive revamping. A first drawback is that the efficiency of the thermal stripping is not optimal, especially in terms of removal of ammonia. Moreover, the relevant ammonia content of the solution discharged by the stripper increases the duty of the downstream medium and low-pressure sections. Said medium and low-pressure sections can be a bottleneck when it is desired to increase capacity.

A process for increasing the capacity of a self-stripping urea plant is disclosed in WO 2006/061083 (WO '1083), aimed at avoiding as much as possible the replacement of costly equipment, and providing inter alia that at least a portion of the process stream from the reactor is stripped in a $CO_2$ stripper with the aid of carbon dioxide as stripping gas, and the condensing capacity in the high-pressure section is increased. According to disclosure of WO '1083, this implies that a $CO_2$ stripper is added or the existing thermal or ammonia stripper is converted into a $CO_2$ stripper. Condensing capacity is increased adding a high-pressure scrubber or a second condenser in series or in parallel with the existing one. Alternatively, it is disclosed to increase the condensing capacity of the existing condenser. Provision of a pool condenser, pool reactor or combi-reactor is also suggested to increase the reaction capacity.

The process of WO '1083 is however still expensive, involving the provision of new equipments (new $CO_2$ stripper and/or new condenser) or substantive modification of the existing one(s). It should be noted that the stripper and the condenser are the most expensive items of the high-pressure loop.

SUMMARY OF THE INVENTION

The technical problem of the present invention is to provide further and less expensive process for revamping self-stripping urea plants of the type herein considered.

The problem is solved by a method for revamping a self-stripping urea plant, said plant comprising a high-pressure synthesis reactor receiving an ammonia feed and a carbon dioxide feed, a high-pressure thermal stripping section and a recovery section comprising medium-pressure and low-pressure equipments for carbamate and ammonia recover, and a high-pressure condensation section comprising at least one shell-and-tube horizontal condenser of the-kettle type, the method being characterized by the provision of a flow line adapted to feed, in operation, a minor portion of the total carbon dioxide feed to said stripping section, for use as a stripping agent.

Said minor portion of the total carbon dioxide feed is preferably 20 to 50%. In a preferred embodiment, around 30% of the carbon dioxide feed is sent to the stripper and the remaining around 70% to the reactor.

In a first embodiment of the inventive process, the existing shell-and-tube kettle condenser is maintained. In particular, the existing kettle condenser can be maintained to reduce cost if an increase of the condensation capacity is not desired.

In a second embodiment, the condensing capacity is increased by adding at least one further condenser in parallel or in series with the existing one.

In a third embodiment, the original kettle condenser is removed and replaced with a new vertical condenser of submerged type.

In a realization of said third embodiment, the new vertical condenser is arranged in a raised position with respect to the reactor and the stripping unit, so to allow natural circulation by gravity in the high-pressure loop, if appropriate. A suitable support structure, in this case, is provided for the vertical condenser. In accordance with another preferred realization, the condenser is kept or arranged substantially at the same height as the reactor; a pump is then provided to deliver the condensed recycled carbamate solution to the reactor.

According to still a further embodiment, means are provided to feed a minor portion of gaseous phase containing ammonia and carbon dioxide, coming out from the stripping section, directly to the reactor, while the remaining major portion of said gaseous phase is sent to the condensation section.

The invention has the following advantages. Use of part of the carbon dioxide feed as a stripping agent improves the carbamate stripping process and has been found advantageous also with no increase of the condensing capacity.

In particular, it has been found that efficiency of a conventional self-stripping plant can be improved in a surprisingly manner at a lower cost than prior-art processes involving the necessary provision of new items such as a new stripper and/or condenser.

The provision of a new submerged vertical condenser has the further advantage of an increased production of urea due to conversion of carbamate into urea taking place in the tubes of the condenser. Hence, reaction capacity is increased without modification of the reactor or provision of a more expensive pool condenser.

Another advantage is that the improved stripping reduces the content of ammonia in the urea solution from the stripping section; hence, the duty of the subsequent treatment section is reduced with the effect of a de-bottlenecking of the whole plant.

It should be noted that the above splitting of the total carbon dioxide into a minor part directed to the stripper, preferably around 30%, and the remaining major part to the reactor, has been found particularly advantageous, in embodiments where the existing kettle condenser is maintained, as well as in embodiments where a new condenser is added or the kettle condenser is replaced with a submerged unit, as disclosed above.

An object of the invention is also a plant for the synthesis of urea, comprising a high-pressure loop comprising at least a synthesis reactor receiving an ammonia feed and a carbon dioxide feed, a stripping section comprising at least one thermal stripper and a condensation section comprising at least one carbamate condenser, and further comprising medium-pressure and low-pressure equipments for carbamate and ammonia recover, characterized by a flow line adapted to feed, in operation, a minor portion of the total carbon dioxide feed to said stripping section, for use as a stripping agent.

Another object of the invention is a process for the synthesis of urea in a self-stripping urea plant, where a high-pressure loop receives an ammonia feed and a carbon dioxide feed, said loop comprising a synthesis reactor, a stripping section comprising at least one thermal stripper, and a condensation section comprising at least one carbamate condenser, the process being characterized in that a minor portion of the total carbon dioxide feed to said stripping section, for use as a stripping agent. Said minor part is preferably 20 to 50% and more preferably around 30%.

Further characteristics and advantages of the invention shall become clearer from the following description of some example embodiments, with reference to the attached drawings.

DETAILED DESCRIPTION OF PREFERRED EMBODIMENTS

Figure 1:
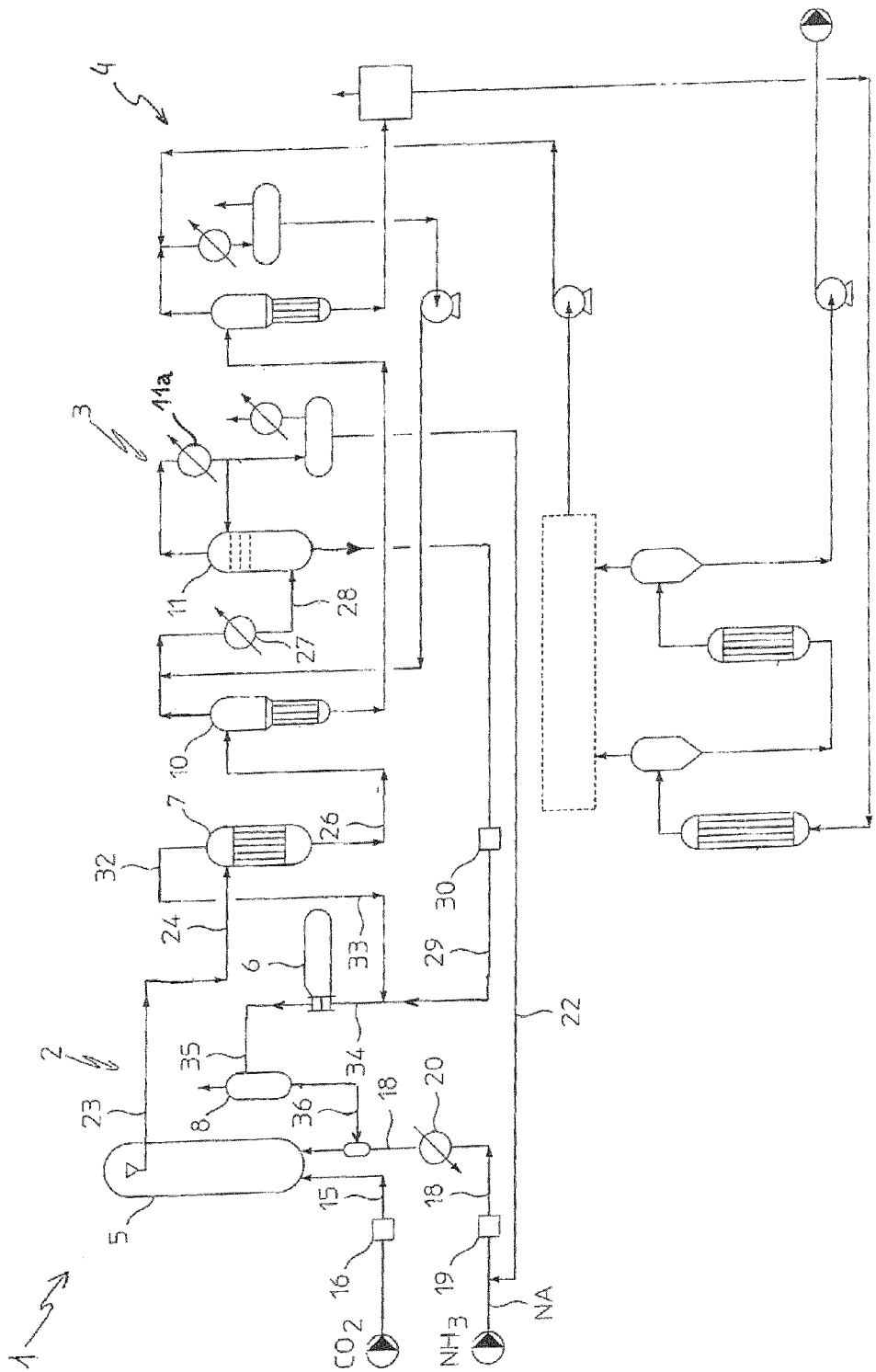
FIG. 1 is a simplified scheme of a conventional self-stripping urea plant.

FIG. 1 is a layout of a conventional self-stripping or thermal stripping urea plant 1. The scheme is simplified and reference will be made only to details which are useful to understand the present invention.

The plant 1 comprises a high-pressure synthesis section or synthesis loop 2 operating for example at around 150 bar; a medium-pressure treatment section 3 operating at 15-25 bars, and a low-pressure urea recovery section 4.

The synthesis loop 2 comprises a reactor 5, a condenser 6 and a stripper 7 operating substantially at the same pressure as well as a scrubber 8.

The condenser 6 is a horizontal shell-and-tube kettle unit receiving an input 34 of carbamate solution from the medium-pressure section via line 29, and gaseous phases discharged by stripper 7 via line 32, 33. Condensation is effected on the tube side, and the condensation heat is used to produce steam.

The stripper 7 is substantially a tube-bundle, steam-heated exchanger. The carbamate solution from reactor 5 forms a liquid film inside the tubes of the tube bundle, whereas the hot steam flowing outside the tubes supplies the heat necessary to decompose the carbamate. Ammonia and carbon dioxide are recovered in gaseous phase at the top of the stripper.

The medium-pressure treatment section 3 comprises a decomposition unit 10 and a rectifying column 11 and ammonia condenser 11a for the recovery of ammonia. The low-pressure treatment section 4 comprises a series of conventional equipments and is not further described.

The means feeding the various flows to the items of plant 1 are generally indicated with 15-36. Such feeding means may comprise connection pipes or ducts, pumps, compressors, ejectors and other known items, and therefore they shall not be described in greater detail. In the present specification, and unless indicated otherwise, the term flow line or line is referred to pipes, ducts, pumps, compressors, ejectors or other known means suitable to convey a liquid or gaseous flow.

The conventional self-stripping plant of FIG. 1, in essential terms, operates as follows. A carbon dioxide feed is sent to the synthesis reactor 5 via line 15 and a compressor 16. Liquid synthesis ammonia is fed to the same reactor 5 via line 18, pump 19 and a pre-heater 20. Ammonia recovered in the low-pressure section 3 is added via line 22 to the fresh ammonia feed. A mixture comprising urea, unconverted carbamate and free ammonia is discharged from reactor 5 to stripper 7 via flow line 23, 24. The solution is then decomposed in the stripper 7, obtaining a mixture of urea, some residual carbamate and ammonia, which is fed to medium-pressure distillation unit 10 via line 26, and gaseous ammonia and carbon dioxide at line 32.

The decomposition unit 10 obtains a further gaseous flow comprising ammonia and carbon dioxide, and an aqueous solution of urea and residual carbamate. Gaseous ammonia and carbon dioxide are mixed with recycled carbamate solution obtained further downstream in the medium pressure section 3, and the resulting mixture is cooled in a heat exchanger 27 and fed via line 28 to the rectifying column 11. The aqueous solution is further treated in the medium-pressure section 3 obtaining a solution with a low carbamate content further treated in the low-pressure section 4. Gaseous ammonia from the rectifying column 11 is then condensed in a series of conventional cooling and compression stages and recycled via line 22 to the ammonia feed of reactor 5.

The carbamate solution obtained in the rectifying column 11 is recycled via pump 30 and line 29 to the carbamate condenser 6, mixed with the gaseous phase at 33, so that the condenser receives a liquid/gas mixture via line 34. The gases (with the exception of the inerts) are subjected to substantially total condensation in said condenser 6 with the carbamate solution acting as condensation liquid. Output of the condenser 6 is a carbamate solution at line 35, that is recycled to the reactor 5 via separator 8 and feeding line 36.

Figure 2:
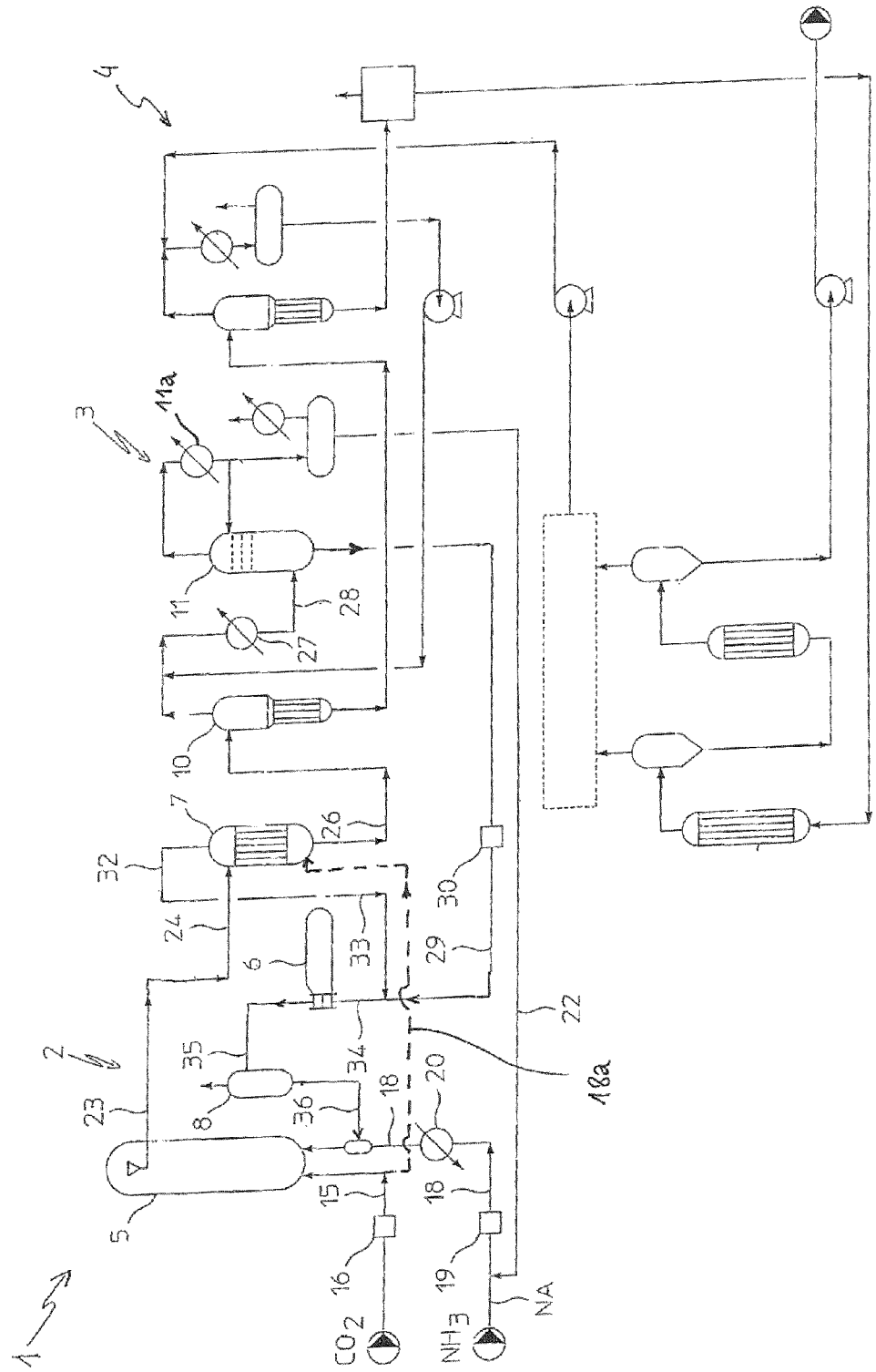
FIG. 2 is a simplified scheme of the plant of FIG. 1, revamped in accordance with an embodiment of the invention.

FIG. 2 is a scheme of the plant 1 revamped in accordance with a first embodiment of the invention. A new carbon dioxide flow line 18a is provided to feed a minor portion of the total carbon dioxide to the stripper 7, for use as a stripping agent. In operation, after the revamping, the portion sent to the stripper 7 via line 18a is a minor portion of the total $CO_2$ feed, preferably between 20% and 50% and more preferably around 30%. The remaining is sent to the reactor 5 via existing line 18. Air can be added advantageously to said line 18 directed to the reactor.

In this first embodiment, no further substantial modification is made to plant 1.

In another embodiment (not shown), the revamping process comprises the further step of providing another condenser added in parallel or in series with the existing kettle condenser 6.

In still another embodiment, the horizontal kettle condenser 6 is replaced with a new vertical submerged condenser, and the flow lines of gaseous ammonia and carbon dioxide from the stripper 7 and recycled carbamate solution are modified so as to feed them to tubes of said new condenser. Details and operation of said new condenser replacing the existing unit 6 may be in accordance with the disclosure of U.S. Pat. No. 7,279,599, which is incorporated herein by reference. In this embodiment, the flow line 33 originally directed to the kettle condenser 6 (FIG. 1) is modified to feed the new submerged condenser.

In all above embodiments, the aqueous solution obtained at the bottom of the stripper 7 has a very low ammonia content, so that the duty of the medium-pressure section 3 and in particular of column 11 and ammonia condenser 11 a is significantly reduced. Duty of the high-pressure ammonia pump 19 is also reduced. This reduction of duty of section 3 and pump 19 is an important advantage of the invention.

In the embodiments where a new vertical submerged condenser is installed, replacing the kettle condenser 6, the new condenser may be arranged in a raised position with respect to the reactor 5 and to the stripper 7 so as to obtain a natural circulation by gravity of the carbamate solution from the condenser to the synthesis reactor 5, and of the aqueous solution comprising urea, carbamate and free ammonia from reactor 5 to stripper 7. In such a case it is preferred to run the reactor at the same pressure of the stripper, to allow said natural circulation.

It is also possible to install said new vertical condenser substantially at the same height as the reactor 5 and the stripper 7. Preferably, a pump is also provided to deliver the carbamate solution from said new condenser to the synthesis reactor 5.

It should be noted that conversion of carbamate into urea takes place also in the tubes of the submerged condenser; it has been found that the urea production of a conventional self-stripping plant can be increased by around 30%, thanks to the adoption of said condenser.

The invention claimed is:

1. A method for revamping a self-stripping urea plant, said plant comprising a high-pressure loop comprising at least a synthesis reactor receiving an ammonia feed and a carbon dioxide feed, a stripping section comprising at least one thermal stripper and a condensation section comprising at least one carbamate condenser, and further comprising medium-pressure and low-pressure equipments for carbamate and ammonia recover, the method comprising providing of a flow line adapted to feed, in operation, a minor portion of the total carbon dioxide feed to said stripping section, for use as a stripping agent.

2. The method according to claim 1, wherein said minor portion of the total carbon dioxide feed, to be used as a stripping agent, is between 20 and 50%.

3. The method according to claim 1, wherein a further condenser is added in parallel or in series with an existing condenser of said self-stripping urea plant.

4. The method according to claim 1, wherein said self-stripping urea plant comprises a horizontal shell-and-tube carbamate condenser, and said condenser is replaced with a submerged vertical condenser.

5. The method according to claim 4, wherein said submerged vertical condenser is arranged in a raised position with respect to the existing reactor and stripper of said urea plant, so as to allow, during operation of the revamped plant, a natural circulation by gravity in said high-pressure loop.

6. The method according to claim 5, wherein a suitable support structure is provided for said condenser arranged in a raised position with respect to the existing reactor and stripper.

7. The method according to claim 4, wherein said submerged vertical condenser is arranged substantially at the same height as the reactor.

8. The method according to claim 7, wherein a pump is installed to deliver the condensed recycled carbamate solution from said condenser to the reactor.

9. The method according to claim 1, characterized by the provision of a flow line adapted to feed a minor portion of a gaseous phase containing ammonia and carbon dioxide, coming out from the stripping section of said plant, directly to the reactor.

10. A process for the synthesis of urea in a self-stripping urea plant, where a high-pressure loop receives an ammonia feed and a carbon dioxide feed, said loop comprising a synthesis reactor, a stripping section comprising at least one thermal stripper, and a condensation section comprising at least one carbamate condenser, the process being characterized in that a minor portion of the total carbon dioxide feed to said stripping section, for use as a stripping agent.

11. The process according to claim 10, where said minor portion is between 20% and 50%.

12. The method according to claim 2, wherein said minor portion of the total carbon dioxide feed, to be used as a stripping agent, is around 30%.

13. The process according to claim 12, where said minor portion is around 30%.

* * * * *